US012780931B2

(12) United States Patent
Park et al.

(10) Patent No.: US 12,780,931 B2
(45) Date of Patent: Nov. 3, 2026

(54) METHODS FOR PURIFYING AN ANTI-4-1BB/ANTI-HER2 BISPECIFIC ANTIBODY

(71) Applicant: YUHAN CORPORATION, Seoul (KR)

(72) Inventors: Ju-Young Park, Seoul (KR); Sung-Hyun Choi, Suwon-si (KR); Yun-Hee Choi, Yongin-si (KR); Won-Tae Kim, Suwon-si (KR)

(73) Assignee: YUHAN CORPORATION, Seoul (KR)

( * ) Notice: Subject to any disclaimer, the term of this patent is extended or adjusted under 35 U.S.C. 154(b) by 633 days.

(21) Appl. No.: 18/273,888

(22) PCT Filed: Jan. 21, 2022

(86) PCT No.: PCT/KR2022/001083

§ 371 (c)(1),
(2) Date: Jul. 24, 2023

(87) PCT Pub. No.: WO2022/158889

PCT Pub. Date: Jul. 28, 2022

(65) Prior Publication Data

US 2024/0084025 A1 Mar. 14, 2024

(30) Foreign Application Priority Data

Jan. 25, 2021 (KR) ........................ 10-2021-0010077

(51) Int. Cl.

| | |
|---|---|
| ***C07K 16/28*** | (2006.01) |
| ***B01D 15/38*** | (2006.01) |
| ***C07K 1/22*** | (2006.01) |
| ***C07K 1/34*** | (2006.01) |
| ***C07K 16/32*** | (2006.01) |

(52) U.S. Cl.

CPC ...... *C07K 16/2878* (2013.01); *B01D 15/3809* (2013.01); *C07K 1/22* (2013.01); *C07K 1/34* (2013.01); *C07K 16/32* (2013.01); *C07K 2317/10* (2013.01); *C07K 2317/31* (2013.01); *C07K 2317/56* (2013.01)

(58) Field of Classification Search

CPC ........ C07K 16/2878; C07K 1/22; C07K 1/34; C07K 16/32; C07K 2317/31; C07K 2317/56; B01D 15/3809

See application file for complete search history.

(56) References Cited

U.S. PATENT DOCUMENTS

| | | | | |
|---|---|---|---|---|
| 10,626,142 | B2 | 4/2020 | Tustian et al. | |
| 10,865,250 | B2 | 12/2020 | Hinner et al. | |
| 2016/0024147 | A1* | 1/2016 | Tustian | C07K 16/065 530/413 |
| 2019/0010248 | A1* | 1/2019 | Hinner | A61P 35/00 |
| 2019/0169308 | A1 | 6/2019 | Dahlen et al. | |
| 2020/0062854 | A1 | 2/2020 | Liu et al. | |
| 2021/0024650 | A1* | 1/2021 | Chung | A61P 35/00 |
| 2021/0198380 | A1 | 7/2021 | Hinner et al. | |
| 2021/0246219 | A1 | 8/2021 | Bruns et al. | |
| 2022/0056136 | A1 | 2/2022 | Park et al. | |
| 2022/0242961 | A1 | 8/2022 | Park et al. | |

FOREIGN PATENT DOCUMENTS

| | | | | |
|---|---|---|---|---|
| WO | 2016/177802 | A1 | 11/2016 | |
| WO | 2018/156740 | A1 | 8/2018 | |
| WO | 2020/043683 | A1 | 3/2020 | |
| WO | WO-2020111913 | A1 * | 6/2020 | A61P 35/00 |
| WO | 2021/020846 | A1 | 2/2021 | |

OTHER PUBLICATIONS

Chen et al., Removing half antibody byproduct by Protein A chromatography during the purification of a bispecific antibody, Protein Expression and Purification, 2020, vol. 172, Issue 105635, 5 pages.

Thermofischer: "Optimizing Protein A Purification of Monoclonal Antibodies When Using the ExpiCHO Expression System I Thermo Fisher Scientific—DE", Jul. 1, 2016 (Jul. 1, 2016), pp. 1-4, XP093215081, Retrieved from the Internet: URL:https://www.thermofisher.com/de/de/home/life-science/protein-biology/protein-biology-learning-center/protein-biology-resource-library/ protein-biology-application-notes/optimizing-protein-a-purification-monoclonal-antibodies.html.

* cited by examiner

*Primary Examiner* — Anand U Desai
*Assistant Examiner* — Andrew T Moehlman
(74) *Attorney, Agent, or Firm* — Vorys, Sater, Seymour and Pease LLP; Mih Suhn Koh

(57) ABSTRACT

Provided is a method for purifying an anti-4-1BB/anti-HER2 bispecific antibody, the method of which includes carrying out affinity chromatography with a sodium acetate buffer containing a certain inorganic salt as an elution buffer. The purification method of the presently claimed subject matter increases the elution of an antibody in the intact form, thereby being able to provide an anti-4-1BB/anti-HER2 bispecific antibody in the intact form in high purity and high yield.

6 Claims, No Drawings

Specification includes a Sequence Listing.

SEQUENCE LISTING

```
<160> NUMBER OF SEQ ID NOS: 17

<210> SEQ ID NO 1
<211> LENGTH: 13
<212> TYPE: PRT
<213> ORGANISM: Artificial Sequence
<220> FEATURE:
<223> OTHER INFORMATION: Synthetic L-CDR1 of anti-4-1BB antibody

<400> SEQUENCE: 1

Ser Gly Ser Ser Ser Asn Ile Gly Asn Asn Tyr Val Thr
1               5                   10
```

<210> SEQ ID NO 2
<211> LENGTH: 7
<212> TYPE: PRT
<213> ORGANISM: Artificial Sequence
<220> FEATURE:
<223> OTHER INFORMATION: Synthetic L-CDR2 of anti-4-1BB antibody

<400> SEQUENCE: 2

```
Ala Asp Ser His Arg Pro Ser
1               5
```

<210> SEQ ID NO 3
<211> LENGTH: 11
<212> TYPE: PRT
<213> ORGANISM: Artificial Sequence
<220> FEATURE:
<223> OTHER INFORMATION: Synthetic L-CDR3 of anti-4-1BB antibody

<400> SEQUENCE: 3

```
Ala Thr Trp Asp Tyr Ser Leu Ser Gly Tyr Val
1               5                   10
```

<210> SEQ ID NO 4
<211> LENGTH: 110
<212> TYPE: PRT
<213> ORGANISM: Artificial Sequence
<220> FEATURE:
<223> OTHER INFORMATION: Synthetic light chain variable region of anti-4-1BB antibody

<400> SEQUENCE: 4

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu
            100                 105                 110
```

<210> SEQ ID NO 5
<211> LENGTH: 5
<212> TYPE: PRT
<213> ORGANISM: Artificial Sequence
<220> FEATURE:
<223> OTHER INFORMATION: Synthetic H-CDR1 of anti-4-1BB antibody

<400> SEQUENCE: 5

```
Ser Tyr Asp Met Ser
1               5
```

<210> SEQ ID NO 6
<211> LENGTH: 17
<212> TYPE: PRT
<213> ORGANISM: Artificial Sequence
<220> FEATURE:
<223> OTHER INFORMATION: Synthetic H-CDR2 of anti-4-1BB antibody

<400> SEQUENCE: 6

Trp Ile Ser Tyr Ser Gly Gly Ser Ile Tyr Tyr Ala Asp Ser Val Lys
1 5 10 15

Gly

<210> SEQ ID NO 7
<211> LENGTH: 12
<212> TYPE: PRT
<213> ORGANISM: Artificial Sequence
<220> FEATURE:
<223> OTHER INFORMATION: Synthetic H-CDR3 of anti-4-1BB antibody

<400> SEQUENCE: 7

Asp Ala Gln Arg Asn Ser Met Arg Glu Phe Asp Tyr
1 5 10

<210> SEQ ID NO 8
<211> LENGTH: 121
<212> TYPE: PRT
<213> ORGANISM: Artificial Sequence
<220> FEATURE:
<223> OTHER INFORMATION: Synthetic heavy chain variable region of anti-4-1BB antibody

<400> SEQUENCE: 8

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Asp Met Ser Trp Val Arg Gln Ala Pro Gly Lys Cys Leu Glu Trp Val
35 40 45

Ser Trp Ile Ser Tyr Ser Gly Gly Ser Ile Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Ala Gln Arg Asn Ser Met Arg Glu Phe Asp Tyr Trp Gly
100 105 110

Gln Gly Thr Leu Val Thr Val Ser Ser
115 120

<210> SEQ ID NO 9
<211> LENGTH: 450
<212> TYPE: PRT
<213> ORGANISM: Artificial Sequence
<220> FEATURE:
<223> OTHER INFORMATION: Synthetic heavy chain of anti-HER2 antibody

<400> SEQUENCE: 9

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

-continued

```
Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 10
<211> LENGTH: 719
<212> TYPE: PRT
<213> ORGANISM: Artificial Sequence
<220> FEATURE:
<223> OTHER INFORMATION: Synthetic heavy chain component of anti-4-1BB/anti-HER2 bispecific antibody

<400> SEQUENCE: 10

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Gly Ser Gly Ser Gly Ser Gly Ser Gly Ser Gly Ser Gly Ser
    450                 455                 460

Gly Ser Gly Ser Gln Ser Val Leu Thr Gln Pro Pro Ser Ala Ser Gly
465                 470                 475                 480

Thr Pro Gly Gln Arg Val Thr Ile Ser Cys Ser Gly Ser Ser Ser Asn
                485                 490                 495

Ile Gly Asn Asn Tyr Val Thr Trp Tyr Gln Gln Leu Pro Gly Thr Ala
            500                 505                 510

Pro Lys Leu Leu Ile Tyr Ala Asp Ser His Arg Pro Ser Gly Val Pro
        515                 520                 525

Asp Arg Phe Ser Gly Ser Lys Ser Gly Thr Ser Ala Ser Leu Ala Ile
    530                 535                 540

Ser Gly Leu Arg Ser Glu Asp Glu Ala Asp Tyr Tyr Cys Ala Thr Trp
545                 550                 555                 560

Asp Tyr Ser Leu Ser Gly Tyr Val Phe Gly Cys Gly Thr Lys Leu Thr
                565                 570                 575

Val Leu Gly Gly Gly Gly Ser Gly Gly Gly Gly Ser Gly Gly Gly Gly
            580                 585                 590

Ser Gly Gly Gly Gly Ser Glu Val Gln Leu Leu Glu Ser Gly Gly Gly
        595                 600                 605

Leu Val Gln Pro Gly Gly Ser Leu Arg Leu Ser Cys Ala Ala Ser Gly
    610                 615                 620

Phe Thr Phe Ser Ser Tyr Asp Met Ser Trp Val Arg Gln Ala Pro Gly
625                 630                 635                 640

Lys Cys Leu Glu Trp Val Ser Trp Ile Ser Tyr Ser Gly Gly Ser Ile
                645                 650                 655

Tyr Tyr Ala Asp Ser Val Lys Gly Arg Phe Thr Ile Ser Arg Asp Asn
            660                 665                 670

Ser Lys Asn Thr Leu Tyr Leu Gln Met Asn Ser Leu Arg Ala Glu Asp
        675                 680                 685

Thr Ala Val Tyr Tyr Cys Ala Arg Asp Ala Gln Arg Asn Ser Met Arg
    690                 695                 700

Glu Phe Asp Tyr Trp Gly Gln Gly Thr Leu Val Thr Val Ser Ser
705                 710                 715


<210> SEQ ID NO 11
<211> LENGTH: 214
<212> TYPE: PRT
<213> ORGANISM: Artificial Sequence
<220> FEATURE:
<223> OTHER INFORMATION: Synthetic light chain of anti-HER2 antibody

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45
```

```
Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 12
<211> LENGTH: 18
<212> TYPE: PRT
<213> ORGANISM: Artificial Sequence
<220> FEATURE:
<223> OTHER INFORMATION: Synthetic peptide linker

<400> SEQUENCE: 12

Gly Ser Gly Ser Gly Ser Gly Ser Gly Ser Gly Ser Gly Ser Gly Ser
1               5                   10                  15

Gly Ser


<210> SEQ ID NO 13
<211> LENGTH: 20
<212> TYPE: PRT
<213> ORGANISM: Artificial Sequence
<220> FEATURE:
<223> OTHER INFORMATION: Synthetic peptide linker

<400> SEQUENCE: 13

Gly Gly Gly Gly Ser Gly Gly Gly Gly Ser Gly Gly Gly Gly Ser Gly
1               5                   10                  15

Gly Gly Gly Ser
            20


<210> SEQ ID NO 14
<211> LENGTH: 448
<212> TYPE: PRT
<213> ORGANISM: Artificial Sequence
<220> FEATURE:
<223> OTHER INFORMATION: Synthetic heavy chain  of anti-4-1BB antibody

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

-continued

```
Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Asn Ser Met Arg Glu Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445
```

<210> SEQ ID NO 15
<211> LENGTH: 121
<212> TYPE: PRT
<213> ORGANISM: Artificial Sequence
<220> FEATURE:
<223> OTHER INFORMATION: Synthetic heavy chain variable region of anti-4-1BB antibody

<400> SEQUENCE: 15

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Asn Ser Met Arg Glu Phe Asp Tyr Trp Gly
            100                 105                 110

Gln Gly Thr Leu Val Thr Val Ser Ser
        115                 120
```

<210> SEQ ID NO 16
<211> LENGTH: 216
<212> TYPE: PRT
<213> ORGANISM: Artificial Sequence
<220> FEATURE:
<223> OTHER INFORMATION: Synthetic light chain of anti-4-1BB antibody

<400> SEQUENCE: 16

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
```

-continued

```
            180                 185                 190

Arg Ser Tyr Ser Cys Gln Val Thr His Glu Gly Ser Thr Val Glu Lys
        195                 200                 205

Thr Val Ala Pro Ala Glu Cys Ser
    210                 215


<210> SEQ ID NO 17
<211> LENGTH: 110
<212> TYPE: PRT
<213> ORGANISM: Artificial Sequence
<220> FEATURE:
<223> OTHER INFORMATION: Synthetic light chain variable region of
      anti-4-1BB antibody

<400> SEQUENCE: 17

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu
            100                 105                 110
```

METHODS FOR PURIFYING AN ANTI-4-1BB/ANTI-HER2 BISPECIFIC ANTIBODY

SEQUENCE LISTING

The Sequence Listing submitted in text format (.txt) filed on Jul. 24, 2023, named "SequenceListing.txt", created on Jul. 21, 2023 (22.8 KB), is incorporated herein by reference.

TECHNICAL FIELD

The present invention relates to a method for purifying an anti-4-1BB/anti-HER2 bispecific antibody. More specifically, the present invention relates to a method for purifying an anti-4-1BB/anti-HER2 bispecific antibody, the method of which comprises carrying out affinity chromatography with a sodium acetate buffer containing a certain inorganic salt as an elution buffer.

BACKGROUND ART 4-1BB protein is a member of TNF-receptor superfamily (TNFRSF) and is a co-stimulatory molecule which is expressed following the activation of immune cells, both innate and adaptive immune cells. 4-1BB plays important role in modulate the activity of various immune cells. 4-1BB agonists enhance proliferation and survival of immune cells, secretion of cytokines, and cytolytic activity CD8 T cells. Therefore, 4-1BB may be a promising target molecule in cancer immunology. Despite of their anti-tumor efficacy, anti-4-1BB antibody induced severe liver toxicity in clinical application.

HER2, which is a receptor tyrosine kinase (RTK) present on the surface of cells, induces proliferation and penetration of cancer cells, angiogenesis, etc.

Multispecific antibodies targeting two or more antigens are expected as a new drug having excellent therapeutic effects compared to a monoclonal antibody. A multispecific antibody capable of recognizing two different antigens wherein one is present on a cancer cell and the other is present on an immune cell can induce more potent cancer-specific immune responses. The present applicant has developed various antibodies that specifically bind to both 4-1BB and HER2, i.e., anti-4-1BB/anti-HER2 bispecific antibodies (International Patent Application No. PCT/KR2020/009871). The anti-4-1BB/anti-HER2 bispecific antibodies activate 4-1BB signaling and boost strong immune cells only in presence of HER2 expressing cells. Therefore, due to said specific HER2-mediated immune response, it is expected to have much less liver toxicity by using the bispecific antibodies compared to 4-1BB monoclonal antibody. The International Patent Application No. PCT/KR2020/009871 is incorporated herein by reference.

DISCLOSURE

Technical Problem

The present inventors recognized a problem that, when anti-4-1 BB/anti-HER2 bispecific antibody-producing cells were cultured and the anti-4-1BB/anti-HER2 bispecific antibodies were isolated therefrom according to the disclosures of International Patent Application No. PCT/KR2020/009871, the resulting antibodies in a significant amount are present in the form of aggregates. The present inventors carried out various studies to develop a purification method capable of increasing the purity of the anti-4-1BB/anti-HER2 bispecific antibody in the intact form. As the results thereof, it has been found that, when affinity chromatography is performed with a sodium acetate buffer containing a certain inorganic salt as an elution buffer, the anti-4-1BB/anti-HER2 bispecific antibody in the intact form can be obtained in high purity and high yield.

Therefore, it is an object of the present invention to provide a method for purifying an anti-4-1BB/anti-HER2 bispecific antibody, the method of which comprises carrying out affinity chromatography with a sodium acetate buffer containing a certain inorganic salt as an elution buffer.

Technical Solution

In accordance with an aspect of the present invention, there is provided a method for purifying an anti-4-1BB/anti-HER2 bispecific antibody, the method of which comprises (a) filtering a culture supernatant of an anti-4-1BB/anti-HER2 bispecific antibody-producing cell line to obtain a crude antibody-containing filtrate; (b) loading the filtrate onto a protein A affinity chromatography column; and (c) eluting the antibody from the column of step (b) with a sodium acetate buffer containing $CaCl_2$.

In the purification method of the present invention, the heavy chain of the anti-4-1BB/anti-HER2 bispecific antibody comprises (i) a heavy chain of anti-HER2 antibody consisting of the amino acids of SEQ ID NO: 9 and (ii) a scFv of anti-4-1BB antibody comprising a light chain variable region of anti-4-1BB antibody comprising the amino acids of SEQ ID NOs: 1, 2, and 3; and a heavy chain variable region of anti-4-1BB antibody comprising the amino acids of SEQ ID NOs: 5, 6, and 7, and the light chain of the anti-4-1BB/anti-HER2 bispecific antibody comprises a light chain of anti-HER2 antibody consisting of the amino acids of SEQ ID NO: 11.

In an embodiment, the light chain variable region of anti-4-1BB antibody may consist of the amino acids of SEQ ID NO: 4; and the heavy chain variable region of anti-4-1BB antibody may consist of the amino acids of SEQ ID NO: 8. In another embodiment, the scFv of anti-4-1BB antibody may further comprise a linker consisting of the amino acids of SEQ ID NO: 13. In still another embodiment, the heavy chain of the anti-4-1BB/anti-HER2 bispecific antibody may further comprise (iii) a linker consisting of the amino acids of SEQ ID NO: 12. In still another embodiment, the heavy chain of the anti-4-1BB/anti-HER2 bispecific antibody may consist of the amino acids of SEQ ID NO:

In the purification method of the present invention, $CaCl_2$ may be present in a concentration ranging from 30 to 500 mM, preferably from 75 to 125 mM, in the sodium acetate buffer. And, sodium acetate may be present in a concentration ranging from 20 to 100 mM in the sodium acetate buffer. In addition, the sodium acetate buffer may have a pH ranging from pH 3.5 to pH 4.0.

Advantageous Effects

When affinity chromatography is performed with a sodium acetate buffer containing a certain inorganic salt, i.e., $CaCl_2$, as an elution buffer according to the present invention, the elution of an antibody in the intact form can be remarkably increased, thereby being able to provide an anti-4-1BB/anti-HER2 bispecific antibody in the intact form in high purity and high yield. Therefore, the purification method of the present invention can provide the anti-4-1BB/anti-HER2 bispecific antibody in high purity and high yield.

BEST MODE

The present invention provides a method for purifying an anti-4-1BB/anti-HER2 bispecific antibody, the method of which comprises (a) filtering a culture supernatant of an anti-4-1BB/anti-HER2 bispecific antibody-producing cell line to obtain a crude antibody-containing filtrate; (b) loading the filtrate onto a protein A affinity chromatography column; and (c) eluting the antibody from the column of step (b) with a sodium acetate buffer containing $CaCl_2$.

In the purification method of the present invention, the anti-4-1 BB/anti-HER2 bispecific antibody consists of a heavy chain and a light chain, which may be prepared as disclosed in International Patent Application No. PCT/KR2020/009871. Specifically, the heavy chain of the anti-4-1BB/anti-HER2 bispecific antibody comprises (i) a heavy chain of anti-HER2 antibody consisting of the amino acids of SEQ ID NO: 9 and (ii) a scFv (single-chain Fv) of anti-4-1BB antibody comprising a light chain variable region of anti-4-1BB antibody comprising the amino acids of SEQ ID NOs: 1, 2, and 3; and a heavy chain variable region of anti-4-1BB antibody comprising the amino acids of SEQ ID NOs: 5, 6, and 7, and the light chain of the anti-4-1BB/anti-HER2 bispecific antibody comprises a light chain of anti-HER2 antibody consisting of the amino acids of SEQ ID NO: 11.

In an embodiment, the light chain variable region of anti-4-1BB antibody may consist of the amino acids of SEQ ID NO: 4 and the heavy chain variable region of anti-4-1BB antibody may consist of the amino acids of SEQ ID NO: 8. In another embodiment, the scFv of anti-4-1BB antibody may further comprise a linker consisting of the amino acids of SEQ ID NO: 13. For example, the scFv of anti-4-1BB antibody may be a polypeptide in which the amino acids of SEQ ID NO: 4, the amino acids of SEQ ID NO: 13, and the amino acids of SEQ ID NO: 8 are linked in sequence (i.e., N'→C').

In an embodiment, the heavy chain of the anti-4-1BB/anti-HER2 bispecific antibody may further comprise (iii) a linker consisting of the amino acids of SEQ ID NO: 12. For example, the heavy chain of the anti-4-1BB/anti-HER2 bispecific antibody may be a polypeptide in which the amino acids of SEQ ID NO: 9, the amino acids of SEQ ID NO: 12, the amino acids of SEQ ID NO: 4, the amino acids of SEQ ID NO: 13, and the amino acids of SEQ ID NO: 8 are linked in sequence (i.e., N'→C'), i.e., a polypeptide consisting of the amino acids of SEQ ID NO: 10.

The purification method of the present invention includes filtering a culture supernatant of an anti-4-1BB/anti-HER2 bispecific antibody-producing cell line to obtain a filtrate containing a crude antibody [step (a)]. The anti-4-1BB/anti-HER2 bispecific antibody-producing cell line may be cells (e.g., CHO cells) transfected with the plasmid(s) into which polynucleotides encoding the heavy and light chains of the anti-4-1BB/anti-HER2 bispecific antibody respectively are inserted. Said transfected cells may be obtained as disclosed in International Patent Application No. PCT/KR2020/009871. The transfected cells may be cultured in a medium conventionally used in the field of biotechnology according to a conventional method. The culture supernatant may be obtained e.g., by centrifuging a culture of the anti-4-1BB/anti-HER2 bispecific antibody-producing cell line. The filtering may be carried out according to a conventional aseptic filtration, e.g., an aseptic filtration through a 0.2 μm membrane filter. The crude antibody-containing filtrate obtained as described above includes about 40 to 45% of antibody aggregates.

The purification method of the present invention includes loading the filtrate obtained in step (a) onto a protein A affinity chromatography column [step (b)]. The protein A affinity chromatography includes the use of various agarose-based resins. As the resin, there may be used known agarose-based resins, for example, affinity chromatography resins such as MabSelect SuRe™ LX (Cytiva), MabSelect™ PrismA (Cytiva), Praesto™ jetted A50 (Purolite Life Sciences), etc., preferably MabSelect™ PrismA (Cytiva). Loading the filtrate obtained in step (a) onto a protein A affinity chromatography column filled with e.g., MabSelect™ PrismA (Cytiva) resins may be carried out according to a conventional method. For example, the filtrate may be loaded at a rate of 20 to 40 mg per ml of resin, but is not limited thereto.

The purification method of the present invention includes eluting the antibody (i.e., an anti-4-1BB/anti-HER2 bispecific antibody) from the column of step (b) with a sodium acetate buffer containing $CaCl_2$ as an elution buffer [step (c)]. The $CaCl_2$ may be present preferably in a concentration ranging from 30 to 500 mM, more preferably in a concentration ranging from 50 to 500 mM, still more preferably in a concentration ranging from 75 to 125 mM, particularly preferably in a concentration of about 100 mM, in the sodium acetate buffer. The sodium acetate may be present preferably in a concentration ranging from 20 to 100 mM in the sodium acetate buffer. In an embodiment of the present invention, $CaCl_2$ may be present in a concentration ranging from 75 to 125 mM in the sodium acetate buffer and sodium acetate may be present in a concentration ranging from 20 to 100 mM in the sodium acetate buffer.

The sodium acetate buffer may have preferably a pH ranging from pH 3.5 to pH 4.0, more preferably a pH of about pH 3.7. In an embodiment of the present invention, $CaCl_2$ may be present in a concentration ranging from 75 to 125 mM in the sodium acetate buffer; sodium acetate may be present in a concentration ranging from 20 to 100 mM in the sodium acetate buffer; and the sodium acetate buffer may have a pH ranging from pH 3.5 to pH 4.0.

In an embodiment of the purification method according to the present invention, the sodium acetate buffer may be a 100 mM sodium acetate buffer containing about 100 mM $CaCl_2$) and having a pH of about pH 3.7.

In another embodiment of the purification method according to the present invention, the sodium acetate buffer may be a 20 mM sodium acetate buffer containing about 100 mM $CaCl_2$ and having a pH of about pH 3.7.

The anti-4-1BB/anti-HER2 bispecific antibody obtained according to the purification method of the present invention may be isolated in the form of an antibody-containing solution from the eluted solution of step (c) by carrying out virus inactivation and neutralization processes according to conventional methods. The virus inactivation may be carried out, e.g., by adjusting the pH to a pH of 3.4 to 3.6 and the neutralization may be carried out, e.g., by using a 1M tromethamine solution, but is not limited thereto. If necessary, after performing the process of step (c), there may be additionally carried out one or more chromatography selected from the group consisting of cation exchange chromatography, anion exchange chromatography, mixed-mode chromatography, and hydrophobic interaction chromatography.

The present invention will be described in further detail with reference to the following preparation examples and examples. These preparation examples and examples are for illustrative purposes only and are not intended to limit the scope of the present invention.

Preparation Example: Preparation of Anti-4-1BB/Anti-HER2 Bispecific Antibody

In accordance with the methods disclosed in International Patent Application No. PCT/KR2020/009871, an anti-4-1BB/anti-HER2 bispecific antibody was prepared as follows.

(1) Anti-4-1BB scFv Antibody

Screening was carried out by phage library immunotube panning against 4-1BB. For panning of the phage library (obtained from KBio Health and CUREBIO) against the target molecule, four rounds of panning were carried out in total using human 4-1BB (NCBI Accession No. NP_001552.2) coated immunotubes.

Bacterial colonies from the 3 rounds of panning output were grown in SB-Carbenicillin (Biomatik cat #A2311-5g) in 96 deepwell plate until turbid, at which point $10^{11}$ pfu of VCSM13 helper phage (K-Bio Health) was added to each well. After 1 hour infection at 37° C. with gentle shaking (80 rpm), 70 μg/mL of kanamycin was added and the cells were cultured overnight at 30° C. with shaking at 200 rpm.

Next day, the plates were centrifuged and the supernatants containing the phages were added to 4-1BB antigen-coated ELISA plates blocked with 3% (v/v) BSA (bovine serum albumin) in PBST (Phosphate Buffered Saline with Tween® 20 (polysorbate 20)). After 1 hour incubation at room temperature, the plates were washed three times with PBST and anti-M13 antibody (Sino Biological cat #11973-MM05) was added. The plates were incubated for 1 hour, washed three times with PBST, and the binding activity was measured using tetramethylbenzidine (TMB).

The 4-1BB specific binders were amplified for plasmid DNA sequencing. The light chain- and heavy chain-variable region (VL and VH) sequences were analyzed to identify unique sequences and determine sequence diversity. The anti-4-1BB antibody indicated as BMUR (BMS's Urelumab, U.S. Pat. No. 7,288,638) is used for comparing agonistic activity. As the results thereof, the sequences of the full human monoclonal antibody against 4-1BB are as follows.

TABLE 1

| | Amino acid sequences (N'→C') |
|---|---|
| Heavy chain | EVQLLESGGGLVQPGGSLRLSCAASGFTFSSYDMSWVRQAPGKGLE WVSWISYSGGSIYYADSVKGRFTISRDNSKNTLYLQMNSLRAEDTAV YYCARDAQRNSMREFDYWGQGTLVTVSSASTKGPSVFPLAPCSRST SESTAALGCLVKDYFPEPVTVSWNSGALTSGVHTFPAVLQSSGLYSL SSVVTVPSSSLGTKTYTCNVDHKPSNTKVDKRVESKYGPPCPPCPAP EFLGGPSVFLFPPKPKDTLMISRTPEVTCVVVDVSQEDPEVQFNWYV DGVEVHNAKTKPREEQFNSTYRVVSVLTVLHQDWLNGKEYKCKVSN KGLPSSIEKTISKAKGQPREPQVYTLPPSQEEMTKNQVSLTCLVKGFY PSDIAVEWESNGQPENNYKTTPPVLDSDGSFFLYSRLTVDKSRWQE GNVFSCSVMHEALHNHYTQKSLSLSLGK (SEQ ID NO: 14) |
| Heavy chain variable region (VH) | EVQLLESGGGLVQPGGSLRLSCAASGFTFSSYDMSWVRQAPGKGLE WVSWISYSGGSIYYADSVKGRFTISRDNSKNTLYLQMNSLRAEDTAV YYCARDAQRNSMREFDYWGQGTLVTVSS (SEQ ID NO: 15) |
| H-CDR1 | SYDMS (SEQ ID NO: 5) |
| H-CDR2 | WISYSGGSIYYADSVKG (SEQ ID NO: 6) |
| H-CDR3 | DAQRNSMREFDY (SEQ ID NO: 7) |
| Light chain | QSVLTQPPSASGTPGQRVTISCSGSSSNIGNNYVTWYQQLPGTAPKL LIYADSHRPSGVPDRFSGSKSGTSASLAISGLRSEDEADYYCATWDY SLSGYVFGGGTKLTVLGQPKAAPSVTLFPPSSEELQANKATLVCLISD FYPGAVTVAWKADSSPVKAGVETTTPSKQSNNKYAASSYLSLTPEQ WKSHRSYSCQVTHEGSTVEKTVAPAECS (SEQ ID NO: 16) |
| Light chain variable region (VL) | QSVLTQPPSASGTPGQRVTISCSGSSSNIGNNYVTWYQQLPGTAPKL LIYADSHRPSGVPDRFSGSKSGTSASLAISGLRSEDEADYYCATWDY SLSGYVFGGGTKLTVL (SEQ ID NO: 17) |
| L-CDR1 | SGSSSNIGNNYVT (SEQ ID NO: 1) |
| L-CDR2 | ADSHRPS (SEQ ID NO: 2) |
| L-CDR3 | ATWDYSLSGYV (SEQ ID NO: 3) |

The anti-4-1BB scFv antibody with a structure of (N')-VL-linker-VH-(C') shown in Table 2 below was prepared using $(GGGGS)_4$ of SEQ ID NO: 13 as a linker, wherein the amino acid residue "G" at the position 103 of the light chain variable region was substituted with "C" (SEQ ID NO: 4) and the amino acid residue "G" at the position 44 of a heavy chain variable region was substituted with "C" (SEQ ID NO: 8), in order to stabilize the scFv by generating a disulfide bridge. Specifically, the polynucleotide in which the DNA encoding the light chain variable region of SEQ ID NO: 4, the DNA encoding the linker of SEQ ID NO: 13, and the DNA encoding the heavy chain variable region of SEQ ID NO: 8 are linked was inserted into pcDNA 3.4 (Invitrogen, A14697). The resulting vector was transfected into ExpiCHO cells (Gibco, A29127) at 37° C. using Expi-Fectamine™ CHO Kit (Gibco, A29133), followed by culturing the cells for 8 days. The culture supernatant was filtered with a 0.2 μm filter to prepare an anti-4-1BB scFv antibody with a structure of (N')-VL-linker-VH-(C').

TABLE 2

| | Amino acid sequences (N'→C') |
|---|---|
| Light chain variable region (VL) | QSVLTQPPSASGTPGQRVTISCSGSSSNIGNNYVTWYQQLPGTAPKLLIYADSHRPSGVPDRFSGSKSGTSASLAISGLRSEDEADYYCATWDYSLSGYVFGCGTKLTVL (SEQ ID NO: 4) |
| Linker | GGGGSGGGGSGGGGSGGGGS (SEQ ID NO: 13) |
| Heavy chain variable region (VH) | EVQLLESGGGLVQPGGSLRLSCAASGFTFSSYDMSWVRQAPGKCLEWVSWISYSGGSIYYADSVKGRFTISRDNSKNTLYLQMNSLRAEDTAVYYCARDAQRNSMREFDYWGQGTLVTVSS (SEQ ID NO: 8) |

(2) Anti-HER2 Antibody

As HER2 targeting moieties for an anti-4-1BB/anti-HER2 bispecific antibody, the heavy and light chains of trastuzumab (Genentech; hereinafter referred to as "HER2 (WT)", DrugBank Accession No. DB00072; human IgG1 Kappa monoclonal antibody) were used. The amino acid sequences of the heavy and light chains of HER2 (WT) are shown in Table 3 below.

TABLE 3

| HER2 (WT) | Amino acid sequences (N'→C') |
|---|---|
| Heavy chain | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 9) |

TABLE 3-continued

| HER2 (WT) | Amino acid sequences (N'→C') |
|---|---|
| Light chain | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 11) |

(3) Anti-4-1BB/Anti-HER2 Bispecific Antibody-Producing Cell Line

Using the anti-4-1BB scFv antibody and the heavy and light chains of HER2 (WT) obtained in (1) and (2) above, we prepared an antibody in the IgG-scFv fusion form (the scFv antibody fragment is fused to the c-terminus of IgG), i.e., an anti-4-1BB/anti-HER2 bispecific antibody having a heavy component consisting of SEQ ID NO: 10 and a light component consisting of SEQ ID NO: 11, as shown in Table 4 below.

Specifically, the DNA segment 2 encoding the GS linker of SEQ ID NO: 12 was fused to the terminus of the DNA segment 1 encoding the heavy chain of anti-HER2 antibody (SEQ ID NO: 9); and then the DNA segment 3 encoding the scFv of anti-4-1BB antibody was fused thereto to prepare a DNA segment encoding the heavy chain of anti-HER2/anti-4-1BB bispecific antibody (SEQ ID NO: 10), which was then inserted into a plasmid 1 (Invitrogen, A14697). In addition, a DNA segment 4 encoding the light chain of anti-HER2/anti-4-1BB bispecific antibody (SEQ ID NO: 11) was inserted into a plasmid 2 (Invitrogen, A14697).

The resulting plasmids 1 and 2 were transfected into ExpiCHO cells (Gibco, A29127) using the ExpiCHO™ Expression System (Gibco, A29133). Specifically, the obtained plasmid 1 (250 μg) and 2 (250 μg) were mixed with OptiPRO™ SFM (12309-050) with ExpiFectamine CHO reagent (A29129) (800 μL) (final volume: 20 mL), followed by being left for 3 minutes. For transfection, the resulting mixed solution and $6\times10^6$ ExpiCHO cells were cultured in a ExpiCHO expression medium (A29100-01) in an 8% $CO_2$ humidified shaking incubator at 37° C. After 18 hours of incubation, 1.5 mL of ExpiFectamine™ CHO Transfection Enhancer 1 and ExpiFectamine™ CHO Feed were added thereto and then the incubation was continued at 37° C. for 4 days. After the temperature was adjusted to 32° C., ExpiFectamine™ CHO Feed was added thereto and then the incubation was continued for 8 days.

TABLE 4

| | | Amino acid sequences (N'→C') |
|---|---|---|
| Heavy | ① Heavy chain of anti-HER2 antibody | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 9) |

TABLE 4-continued

| | | | Amino acid sequences (N'→C') |
|---|---|---|---|
| component | ② Linker | | GSGSGSGSGSGSGSGSGS (SEQ ID NO: 12) |
| | ③ scFv<br>of<br>anti-<br>4-1BB<br>antibody | VL | QSVLTQPPSASGTPGQRVTISCSGSSSNIGNNYVT<br>WYQQLPGTAPKLLIYADSHRPSGVPDRFSGSKSG<br>TSASLAISGLRSEDEADYYCATWDYSLSGYVFGC<br>GTKLTVL (SEQ ID NO: 4)<br>* L-CDR1: SGSSSNIGNNYVT (SEQ ID NO: 1)<br>* L-CDR2: ADSHRPS (SEQ ID NO: 2)<br>* L-CDR3: ATWDYSLSGYV (SEQ ID NO: 3) |
| | | Linker | GGGGGGGGSGGGGSGGGGS (SEQ ID NO: 13) |
| | | VH | EVQLLESGGGLVQPGGSLRLSCAASGFTFSSYDM<br>SWVRQAPGKCLEWVSWISYSGGSIYYADSVKGR<br>FTISRDNSKNTLYLQMNSLRAEDTAVYYCARDAQ<br>RNSMREFDYWGQGTLVTVSS (SEQ ID NO: 8)<br>* H-CDR1: SYDMS (SEQ ID NO: 5)<br>* H-CDR2: WISYSGGSIYYADSVKG<br>(SEQ ID NO: 6)<br>* H-CDR3: DAQRNSMREFDY (SEQ ID NO: 7) |
| | Heavy<br>component<br>(①+ ② + ③) | | EVQLVESGGGLVQPGGSLRLSCAASGFNIKDTYI<br>HWVRQAPGKGLEWVARIYPTNGYTRYADSVKGRF<br>TISADTSKNTAYLQMNSLRAEDTAVYYCSRWGGD<br>GFYAMDYWGQGTLVTVSSASTKGPSVFPLAPSSK<br>STSGGTAALGCLVKDYFPEPVTVSWNSGALTSGV<br>HTFPAVLQSSGLYSLSSVVTVPSSSLGTQTYICN<br>VNHKPSNTKVDKKVEPKSCDKTHTCPPCPAPELL<br>GGPSVFLFPPKPKDTLMISRTPEVTCVVVDVSHE<br>DPEVKFNWYVDGVEVHNAKTKPREEQYNSTYRVV<br>SVLTVLHQDWLNGKEYKCKVSNKALPAPIEKTIS<br>KAKGQPREPQVYTLPPSREEMTKNQVSLTCLVKG<br>FYPSDIAVEWESNGQPENNYKTTPPVLDSDGSFF<br>LYSKLTVDKSRWQQGNVFSCSVMHEALHNHYTQK<br>SLSLSPGKGSGSGSGSGSGSGSGSQSVLTQPP<br>SASGTPGQRVTISCSGSSSNIGNNYVTWYQQLPG<br>TAPKLLIYADSHRPSGVPDRFSGSKSGTSASLAI<br>SGLRSEDEADYYCATWDYSLSGYVFGCGTKLTVL<br>GGGGSGGGGSGGGGSGGGGSEVQLLESGGGLVQ<br>PGGSLRLSCAASGFTFSSYDMSWVRQAPGKCLE<br>WVSWISYSGGSIYYADSVKGRFTISRDNSKNTL<br>YLQMNSLRAEDTAVYYCARDAQRNSMREFDYWG<br>QGTLVTVSS (SEQ ID NO: 10) |
| Light<br>component | Light chain of<br>anti-HER2<br>antibody | | DIQMTQSPSSLSASVGDRVTITCRASQDVNTAVA<br>WYQQKPGKAPKLLIYSASFLYSGVPSRFSGSRSG<br>TDFTLTISSLQPEDFATYYCQQHYTTPPTFGQGTK<br>VEIKRTVAAPSVFIFPPSDEQLKSGTASVVCLLNN<br>FYPREAKVQWKVDNALQSGNSQESVTEQDSKDSTY<br>SLSSTLTLSKADYEKHKVYACEVTHQGLSSPVTK<br>SFNRGEC (SEQ ID NO: 11) |

(4) Fed-Batch Culture for Antibody Expression

After culturing the anti-4-1BB/anti-HER2 bispecific antibody-producing cell line obtained in (3) in a glutamine-free Actipro medium (Hyclone, SH31037.02) for 3 days, fed-batch culture (working volume: 700 ml/2000 ml flask, 37° C., 5% $CO_2$, 130 rpm) was carried out for 14 days, while Cell Boost™ 7a (Hyclone, SH31026.01)/7b supplements (Hyclone, SH31027.01KR) were added every other day. The culture supernatant obtained by centrifuging the culture at about 3000 rpm was filtered with a 0.2 μm membrane filter to obtain a crude antibody-containing filtrate.

Example 1: Purification of Anti-4-1BB/Anti-HER2 Bispecific Antibody by Protein a Affinity Chromatography MabSelect PrismA affinity chromatography resin (Cytiva) was filled into a column having 1.6 cm of diameter and 20 cm of bed height to prepare a protein A affinity chromatography column, which was then equilibrated with 1× phosphate buffered saline (PBS) (pH 7.4). The crude antibody-containing filtrate obtained in Preparation Example (4) was loaded onto the protein A affinity chromatography column at a ratio of 30 mg per mL of resin. After washing the column with 1×PBS (pH 7.4), the antibody was eluted with the sodium acetate buffers containing an excipient ($CaCl_2$) or with the sodium acetate buffer having no excipient as an elution buffer. The concentrations of excipient and sodium acetate in the elution buffer and the pH of the elution buffer are shown in Table 5 below.

For the pools obtained using the respective elution buffers, the yields of the antibody (i.e., anti-4-1BB/anti-HER2 bispecific antibody) were analyzed by measuring UV at 280 nm; and the purities of the antibody (i.e., anti-4-1BB/anti-HER2 bispecific antibody) were analyzed by measuring the contents (%) of high molecular weight aggregates using size exclusion chromatography (SEC-HPLC). The analysis using the SEC-HPLC was carried out using a TOSOH® model TSK-GEL® G3000SW$_{XL}$ column (gel filtration chromatography column). After equilibrating the column by flowing 1× phosphate buffered saline (PBS) (pH 7.4) through the column at a flow rate of 1 ml/min, each eluted fraction (100 ug) was injected thereto so as to perform purity analysis. Purity refers to the purity (%) of the intact form and was calculated by the following equation.

Purity (%)=100−content of high molecular weight aggregates (%)

The results obtained by performing the purifications using a protein A affinity chromatography as described above are shown in Table 5 below.

TABLE 5

| # | Elution buffer | Excipient | Purity (%) | Yield (%) |
|---|---|---|---|---|
| (1) | 100 mM sodium acetate buffer (pH 3.7) | — | 76.2 | 100 |
| (2) | 100 mM sodium acetate buffer (pH 3.7) | $CaCl_2$ (30 mM) | 81.5 | 100 |
| (3) | 100 mM sodium acetate buffer (pH 3.7) | $CaCl_2$ (50 mM) | 82.2 | 100 |
| (4) | 100 mM sodium acetate buffer (pH 3.7) | $CaCl_2$ (100 mM) | 91.0 | 92.1 |
| (5) | 100 mM sodium acetate buffer (pH 3.7) | $CaCl_2$ (200 mM) | 91.4 | 84.6 |
| (6) | 100 mM sodium acetate buffer (pH 3.7) | $CaCl_2$ (500 mM) | 90.9 | 84.2 |
| (7) | 20 mM sodium acetate buffer (pH 3.7) | $CaCl_2$ (30 mM) | 81.0 | 96.8 |
| (8) | 20 mM sodium acetate buffer (pH 3.7) | $CaCl_2$ (50 mM) | 87.5 | 95.7 |
| (9) | 20 mM sodium acetate buffer (pH 3.7) | $CaCl_2$ (100 mM) | 93.0 | 95.5 |
| (10) | 20 mM sodium acetate buffer (pH 3.7) | $CaCl_2$ (200 mM) | 90.1 | 83.2 |

As can be seen from the results in Table 5 above, when the sodium acetate buffers containing $CaCl_2$ were used as an excipient, the purity of anti-4-1BB/anti-HER2 bispecific antibody can be remarkably increased with a relatively high yield. And, from the results in Table 5, it can be seen that the concentration of $CaCl_2$ in the sodium acetate buffer is preferably in the range of 30 to 500 mM, more preferably in the range of 50 to 500 mM, still more preferably in the range of 75 to 125 mM, and particularly preferably about 100 mM. In addition, it can be seen that the concentration of sodium acetate in the sodium acetate buffer is preferably in the range of 20 to 100 mM.

Comparative Example 1: Purification of Anti-4-1BB/Anti-HER2 Bispecific Antibody Using NaCl as an Excipient Purification with protein A affinity chromatography was carried out in the same manner as in Example 1, using 100 mM sodium acetate buffer (pH3.7) containing NaCl at a concentration of 1000 mM as an excipient. For the eluted pool, the purity and yield were analyzed in the same manner as in Example 1. As the results thereof, the purity was relatively increased compared to the purification using 100 mM sodium acetate (pH 3.7) having no excipient, but the yield was significantly reduced to 29.3%.

From the above results, the purity and yield were evaluated by lowering the concentrations of sodium acetate and the excipient (NaCl). That is, purification with protein A affinity chromatography was carried out in the same manner as in Example 1, using 20 mM sodium acetate buffer (pH3.7) containing NaCl at a concentration of 100 mM as an excipient. For the eluted pool, the purity and yield were analyzed in the same manner as in Example 1. As the results thereof, the purity was significantly reduced to 74.2%.

Therefore, the use of a sodium acetate buffer containing NaCl did not show an improved purification effect, in terms of purity and yield.

Comparative Example 2: Purification of Anti-4-1BB/Anti-HER2 Bispecific Antibody Using $MgCl_2$ as an Excipient Purification with protein A affinity chromatography was carried out in the same manner as in Example 1, using 100 mM sodium acetate buffer (pH3.7) containing $MgCl_2$ at a concentration of 1000 mM as an excipient. For the eluted pool, the purity and yield were analyzed in the same manner as in Example 1. As the results thereof, the purity was relatively increased compared to the purification using 100 mM sodium acetate (pH 3.7) having no excipient, but the yield was significantly reduced to 43.9%.

From the above results, the purity and yield were evaluated by lowering the concentrations of sodium acetate and the excipient ($MgCl_2$). That is, purification with protein A affinity chromatography was carried out in the same manner as in Example 1, using 20 mM sodium acetate buffer (pH3.7) containing $MgCl_2$ at a concentration of 100 mM as an excipient. For the eluted pool, the purity and yield were analyzed in the same manner as in Example 1. As the results thereof, the purity was relatively increased compared to the purification as in the purification using a high concentration of sodium acetate/excipient, but the yield was only 66.7%.

Therefore, the use of a sodium acetate buffer containing $MgCl_2$ did not show an improved purification effect, in terms of yield.

The invention claimed is:

1. A method for purifying an anti-4-1BB/anti-HER2 bispecific antibody, the method of which comprises (a) filtering a culture supernatant of an anti-4-1BB/anti-HER2 bispecific antibody-producing cell line to obtain a crude antibody-containing filtrate, wherein the crude antibody-containing filtrate contains the anti-4-1BB/anti-HER2 bispecific antibody in the form of aggregates; (b) loading the filtrate onto a protein A affinity chromatography column; and (c) eluting the antibody from the column of step (b) with a sodium acetate buffer containing $CaCl_2$) in a concentration ranging from 30 to 500 mM to obtain the purified anti-4-1BB/anti-HER2 bispecific antibody, wherein the heavy chain of the anti-4-1BB/anti-HER2 bispecific antibody consists of the amino acid sequence of SEQ ID NO: 10, and the light chain of the anti-4-1BB/anti-HER2 bispecific antibody comprises a light chain of anti-HER2 antibody consisting of the amino acid sequence acids of SEQ ID NO: 11.

2. The method according to claim 1, wherein $CaCl_2$) is present in a concentration ranging from 75 to 125 mM in the sodium acetate buffer.

3. The method according to claim 1, wherein sodium acetate is present in a concentration ranging from 20 to 100 mM in the sodium acetate buffer.

4. The method according to claim 1, wherein the sodium acetate buffer has a pH ranging from pH 3.5 to pH 4.0.

5. The method according to claim 1, wherein $CaCl_2$) is present in a concentration ranging from 75 to 125 mM in the sodium acetate buffer and sodium acetate is present in a concentration ranging from 20 to 100 mM in the sodium acetate buffer.

6. The method according to claim 5, wherein the sodium acetate buffer has a pH ranging from pH 3.5 to pH 4.0.

* * * * *